(12) United States Patent
Oses Fisac et al.

(10) Patent No.: US 7,743,811 B2
(45) Date of Patent: Jun. 29, 2010

(54) SHEET FOR CLOSING ASEPTIC CONTAINERS, ASEPTIC CONTAINER COMPRISING SAID SHEET, AND EQUIPMENT AND METHOD FOR OBTAINING SAID CONTAINER

(75) Inventors: Roberto Oses Fisac, Oñati (ES); Iosu Errasti Iriarte, Oñati (ES); Juan Jose Jauregui Balanzategi, Oñati (ES); Nerea Arbulu Ormaechea, Oñati (ES); Jone Txintxurreta Espinosa, Oñati (ES)

(73) Assignee: Ulma Packaging Technological Center, S. Coop., Onati (ES)

( * ) Notice: Subject to any disclaimer, the term of this patent is extended or adjusted under 35 U.S.C. 154(b) by 0 days.

(21) Appl. No.: 12/442,033

(22) PCT Filed: Sep. 21, 2006

(86) PCT No.: PCT/ES2006/000528

§ 371 (c)(1),
(2), (4) Date: Mar. 19, 2009

(87) PCT Pub. No.: WO2008/034918

PCT Pub. Date: Mar. 27, 2008

(65) Prior Publication Data

US 2009/0301920 A1 Dec. 10, 2009

(51) Int. Cl.
*B32B 37/00* (2006.01)
(52) U.S. Cl. .................... 156/583.1; 156/500; 156/522
(58) Field of Classification Search ............... 156/69, 156/228, 290, 292, 308.2, 308.4, 500, 501, 156/516, 522, 580, 581, 583.1; 53/548, 553, 53/555
See application file for complete search history.

(56) References Cited

U.S. PATENT DOCUMENTS

| | | | | |
|---|---|---|---|---|
| 6,629,602 B1 * | 10/2003 | Heyman | ...................... | 206/438 |
| 6,996,952 B2 * | 2/2006 | Gupta et al. | .................. | 53/434 |
| 7,040,485 B2 * | 5/2006 | Gupta et al. | ............. | 206/484.1 |
| 2002/0119074 A1 * | 8/2002 | McGowan, Jr. | ............... | 422/26 |
| 2003/0183547 A1 * | 10/2003 | Heyman | ...................... | 206/439 |
| 2005/0067312 A1 * | 3/2005 | Gupta et al. | ................ | 206/484 |
| 2005/0241981 A1 * | 11/2005 | Gupta et al. | ............. | 206/524.8 |

FOREIGN PATENT DOCUMENTS

| | | |
|---|---|---|
| EP | 0266688 A2 | 5/1988 |
| EP | 0846445 A1 | 6/1998 |
| EP | 1520795 A1 | 4/2005 |
| WO | 0242164 A2 | 5/2002 |
| WO | 02058746 A1 | 8/2002 |

OTHER PUBLICATIONS

International Search Report from the corresponding PCT/ES06/000528.

* cited by examiner

*Primary Examiner*—James Sells
(74) *Attorney, Agent, or Firm*—Katten Muchin Rosenman LLP

(57) ABSTRACT

The present invention relates to a closing sheet for aseptic containers, aseptic container comprising said sheet, equipment and method for obtaining said container. The closing sheet comprises a first sheet (7) configured to be traversed by ethylene oxide and a second sheet (8) of impermeable material. The first sheet (7) is obtained from a first reel (7') of film of material that is permeable to ethylene oxide and the second sheet (8) is obtained from a second reel (8') of film of impermeable material. The first sheet (7) is longitudinally sealed to the second sheet (8) through a sealing line (18), thus forming a single closing sheet (10).

4 Claims, 5 Drawing Sheets

SHEET FOR CLOSING ASEPTIC CONTAINERS, ASEPTIC CONTAINER COMPRISING SAID SHEET, AND EQUIPMENT AND METHOD FOR OBTAINING SAID CONTAINER

OBJECT OF THE INVENTION

A first aspect of the present invention relates to a closing sheet for aseptic containers, a second aspect relates to an aseptic container comprising said closing sheet for the aseptic safety of the contained product, a third aspect relates to equipment for obtaining said container and finally, a fourth aspect relates to a method for obtaining the container of the invention, being applicable in the industry of pharmaceutical products and medical use products, in which the availability of products such as instruments, garments or dressings that are properly sterilized and free of microorganisms until the time they are used, is required.

BACKGROUND OF THE INVENTION

In the industry of pharmaceutical and medical use products, it is necessary to have containers ensuring suitable asepsis and hygiene conditions for the products that they contain until the time they are used, usually by healthcare personnel and in some cases by the actual patient.

This type of container comprises a body of impermeable material, which is obtained from a reel of multilayer film (for example, of polyester and/or polyurethane), in which housings suitable for the product to be contained are continuously configured, (for example by means of thermoforming, thermoforming with suction, molding, etc) and a closing sheet which is sealed on the edges of the body of impermeable material, the mentioned closing sheet comprising a material that is permeable to ethylene oxide. The closing sheet is obtained from a continuously fed reel of film which is arranged on the housings formed from a reel of multilayer film and after it is sealed, the unitary containers are cut or separated.

The sterilization of this type of container is carried out once the container is hermetically sealed by means of the closing sheet, containing the object or product to be sterilized. Said sterilization is carried out by inserting the container in an asepsis chamber, which is hermetically closed, a bath of the container being carried out by means of the diffusion of ethylene oxide (normally mixed with other gases) in gaseous state. By means of said bath, ethylene oxide penetrates into the container through the sheet that is permeable thereto and sterilizes its interior, as well as the product contained in the container, eliminating possible microbes and spores.

The atmosphere of the chamber is then stabilized so that the application of ethylene oxide acts suitably for a certain time, and the gas is then extracted or evacuated from the chamber, for example by means of gas absorbers or exhausters, a completely impermeable container the interior of which is suitably sterilized thus being obtained.

The previously described sterilization process is common to many types of aseptic containers for containing medical or pharmaceutical products or objects.

In the containers described in the previous paragraph, as has been indicated, the material that is permeable to ethylene oxide is in the closing sheet of the container, there being currently two types of containers, according to the arrangement of said permeable material and the process for obtaining the closing sheet.

On one hand, there are containers in which the closing sheet is obtained directly from a reel of material that is permeable to ethylene oxide, such that the entire surface of the closing sheet is made of material that is permeable to ethylene oxide, which involves an unnecessary cost increase of the container due to the fact that the cost of said material is much higher than that of the multilayer material in which the body of the container is manufactured.

On the other hand, there are containers in which both the body and the closing sheet are manufactured from a reel of multilayer film (for example of polyester and polypropylene), an inner portion of the closing sheet being cut once the closing sheet has been sealed on the corresponding body of the container, the material that is permeable to ethylene oxide being arranged in the space freed up by said cut, by means of heat sealing.

The aseptic container AMCOR®, corresponding to the multinational company DUPONT®, can be mentioned as a commercial example of this type of container, which container comprises the use of TYBET® sheets of material that is permeable to ethylene oxide, which are used to handle a large variety of sterile products in the medical and pharmaceutical sector, achieving a suitable protection of the contained product, such as for example gowns or any type of disposable medical garment, thus increasing the life and the hygienic conditions of the content of the container during its packaged period.

The problem of this type of container is that it requires the use of an expensive and complex machine and it furthermore increases the waste of multilayer film.

DESCRIPTION OF THE INVENTION

A first aspect of the present invention relates to a closing sheet for aseptic containers, for sealing an interior of said containers which contain objects for medical and/or pharmaceutical use. The closing sheet is obtained from a first reel of film of material that is permeable to ethylene oxide and from a second reel of film of impermeable material, both of which are continuously fed, which are longitudinally heat sealed in a sealing line. The closing sheet will be joined, by heat sealing, to the body of the corresponding container through perimetric edges.

The closing sheet, once it has been sealed on the corresponding container and cut to individualize the container, is formed by a first sheet configured to be traversed by ethylene oxide and a second sheet of impermeable material, a first edge of the first sheet being overlapped with a first edge of the second sheet, forming the mentioned sealing line, the closing sheet comprising perimetric edges formed by a second edge of the first sheet and a second edge of the second sheet.

The sealing line can be straight, circular, crooked, etc., and the closing sheet can have a surface coinciding with a parallelogram, which can be elliptical, circular, etc.

The closing sheet can have a notch to facilitate its opening, or can incorporate (zipper type) opening and closing means which allow re-using the container.

The second sheet can be formed from a multilayer film, for example of polyester and/or polypropylene.

The closing sheet can comprise a printed mark for identifying the container.

A second aspect of the invention relates to an aseptic container comprising a closing sheet like the one described above for containing sterilized objects for medical and/or pharmaceutical use, comprising a body of impermeable material, with the usual barrier characteristics and with a high micronage, defining a housing configured to contain an object, preferably a unitary container, free of microorganisms and spores (in the suitable percentage to obtain asepsis).

According to the invention, the closing sheet is configured to seal the housing defined by the body of the container, the mentioned perimetric edges of said closing sheet being heat sealed to outer edges of the body (1) of the container in its entire perimeter, and said perimetric edges being formed by second perimetric edges corresponding to the first sheet and by second perimetric edges corresponding to the second sheet.

The possibility is contemplated that the body of the container is configured to be obtainable from a multilayer sheet (for example of polyester and/or polypropylene) of plastic, the housing configured to obtain the object being defined by means of thermoforming said multilayer sheet, by means of thermoforming with suction or by molding. It is also possible for the body of the container to be pre-manufactured in an independent machine for its insertion in the automatic equipment making the container, by means of the closing the mentioned body with the closing sheet obtained.

The second sheet is made of a material enabling its welding to the body of the container, (for example, with a layer of polyethylene for sealing) and will preferably be made of the same material as the body.

The surface of the first sheet is configured to allow a passage of an amount of ethylene oxide sufficient to sterilize the housing and the object contained in the container.

The possibility is contemplated that the aseptic container comprises easy opening means existing in the containers of the state of the art configured to allow a removal of the closing sheet by a user without additional means for opening the container.

The aseptic container can comprise an identifying mark for identifying the object contained in the container. It is also provided that the identifying mark is made in the container and in the closing sheet, depending on the technology used for the printing (ink, laser, etc.) and on the nature and characteristics of the material of the body of the container and of the closing sheet.

The problems of this type of closing sheet, formed by two sheets of different material, is that the impermeable material and the material that is permeable to ethylene oxide have a different behavior with regard to their melting point and to their deformation due to stress, therefore, in the event of heat welding at a suitable temperature for the impermeable material, the part of material that is permeable to ethylene oxide is not correctly welded, with the appearance of wrinkles, whereas in the event that the temperature is the suitable one for heat welding the permeable material, there is then an excessive deformation of the impermeable material, whereby a correct sealing of the container is not achieved.

The closing sheet for aseptic containers, the aseptic container comprising said sheet, the equipment and the method for obtaining said container proposed by the invention allows solving the problems set forth above, in the line of heat sealing the closing sheet to the body of the container, taking into consideration the melting points of each material.

The sealing is thus carried out by means of two sealing molds which seal at different temperature and pressure, and therefore undergo different deformations, each temperature being adapted to the nature of the material to be sealed. In the event of using materials of similar sealing temperatures, a single sealing mold could be used.

Since the elasticity of the impermeable material is greater than the material that is permeable to ethylene oxide, for the purpose of preventing deformations in the packaging process and preventing the closing sheet from being wrinkled or deformed, before heat sealing the closing sheet to the body of the container, making weld points (one weld point per container) between a part of the second sheet of impermeable material of the closing sheet and the body of the container is contemplated, the deformation of the closing sheet thus being prevented.

A third aspect of the invention relates to equipment for obtaining an aseptic container described above, comprising:
 a frame,
 a lower reel comprising a film of impermeable material configured to obtain a containing body of the container,
 a plurality of clamps configured to hold two opposite perimetric edges of a sheet of the material of the lower reel.
 A forming mold configured to thermoform a housing in the impermeable material which will form the body of the container.

Likewise, the equipment can comprises at lest one vacuum pump configured to perform vacuum in a face of the body opposite to the closing sheet.

The equipment also comprises:
 a first reel comprising a film of material that is permeable to ethylene oxide,
 a second reel comprising a film of impermeable material,
 sealing jaws configured to heat seal a longitudinal edge of the film of permeable material of the first reel to a longitudinal edge of the film of impermeable material of the second reel, through a sealing line, to form a closing sheet comprising a first sheet of material that is permeable to ethylene oxide and a second sheet of impermeable material, the first and the second sheet being joined through a first edge forming the mentioned sealing line
 a welding device configured to heat weld the film of impermeable material of the second reel, in a plurality of weld points (one point per container), to the film of impermeable material configured to obtain a containing body of the container, in an outer edge of the mentioned body of the container, to prevent ripples and wrinkles in the film,
 a first sealing mold configured to heat seal the first sheet to the outer edges of the body through a first area at a first sealing temperature,
 a second sealing mold configured to heat seal the second sheet to the outer edges of the body through a second area at a second sealing temperature different from the first sealing temperature.

The equipment can comprise a side cutting module configured to cut surplus sides of the closed container, a longitudinal cutting module configured to cut surplus longitudinal edges of the closed container, a device configured to collect the surplus of film of the process and at least one conveyor belt configured to move the obtained containers in the equipment.

The first sealing mold is configured to heat seal the second edges of the first sheet to outer edges of the body of the container and the second sealing mold is configured to heat seal the perimetric edges of the closing sheet to the outer edges of the body of the container. In the second sealing mold, the second edges of the second sheet are heat sealed and the second edges of the first sheet are heat sealed again. The possibility is contemplated that the second sealing mold can only heat seal the second edges of the second sheet. This heat sealing could be carried out simultaneously or sequentially with the heat sealing of the first sealing mold. When the sealing temperatures and the properties of deformation due to stress are similar for the first sheet and the second sheet, the heat sealing can be carried out in a single sealing mold.

Finally, a fourth aspect of the invention relates to a method for obtaining an aseptic container described above with equipment like that described above, comprising the following steps:

- holding with a plurality of clamps two opposite perimetric edges of a film of impermeable material comprised in a lower reel,
- thermoforming a housing in the sheet of impermeable material forming a body,
- arranging an object to be packaged in the housing,
- heat sealing by means of sealing jaws a longitudinal edge of a film of material that is permeable to ethylene oxide, comprised in a first reel, to a longitudinal edge of a film of impermeable material, comprised in a second reel, through a sealing line, forming a closing sheet comprising a first sheet of material that is permeable to ethylene oxide and a second sheet of impermeable material, the first and the second sheet being joined by the overlapping of a first edge of the first and second sheets forming the mentioned sealing line
- heat welding in a plurality of weld points (one point per container) the film of impermeable material of the second reel with the film of impermeable material of the lower reel, in an outer edge of the body of the container,
- heat sealing, in a first sealing mold, a second edge of the first sheet to the outer edges of the body of the container, through a first area, at a first sealing temperature,
- heat sealing, in a second sealing mold, the perimetric edges of the closing sheet to the outer edges of the body of the container at a second sealing temperature different from the first sealing temperature, comprising the heat sealing of the second edge of the second sheet and the heat sealing (it is heat sealed again) of the second edge of the first sheet. The heat sealing in the second sealing mold can comprise only the heat sealing of the second edge of the second sheet to the outer edges of the body of the container, through a second area, at a second sealing temperature different from the first sealing temperature.

It is contemplated as a possibility that the method comprises heat sealing the first sheet to the outer edges and the second sheet to the outer edges simultaneously.

Likewise, after heat sealing the closing sheet to the body, the method can comprise the following steps:

- cutting surplus sides of the container in a side cutting module,
- cutting surplus longitudinal edges of the container in a longitudinal cutting module,
- collecting the surplus of the impermeable film and of the film that is permeable to ethylene oxide Finally, the aseptic container can be marked with an identifying mark for identifying the object contained in the container.

The container can furthermore be obtained, manufactured in automatic packaging lines or equipment existing in the state of the art, allowing a quick and efficient adjustment of the production.

The container obviously complies with its function of keeping the object contained therein in hermetic conditions.

The container and the method proposed by the invention are cheaper than current containers and methods due to the fact that a smaller amount of material that is permeable to ethylene oxide is used, the cost of which is much higher than the rest of the material of the container.

The equipment for obtaining the container is simpler than the equipment necessary for manufacturing the containers of the state of the art which have a window of permeable material in the closing sheet, having in turn a higher production capacity, further allowing a suitable control of the formation of wrinkles and deformation in the lid of the container.

Finally, the equipment allows obtaining different container formats with a minimal number of changes, in molds and jaws, not being restricted to fixed container dimensions, all of this in different types of automatic packaging equipment by means of thermoforming and heat sealing.

DESCRIPTION OF THE DRAWINGS

To complement the description which is being made and with the aim of aiding to better understand the features of the invention according to a preferred practical embodiment thereof, a set of drawings is attached as an integral part said description in which the following has been depicted with an illustrative and non-limiting character.

PREFERRED EMBODIMENT OF THE INVENTION

In view of the indicated figures, it can be observed how in one of the possible embodiments of the invention, a first aspect of the invention relates to a closing sheet for aseptic containers, for sealing an interior of said containers which contain objects for medical and/or pharmaceutical use, comprising a first sheet (7) configured to be traversed by ethylene oxide and a second sheet (8) of impermeable material.

Figure 4:
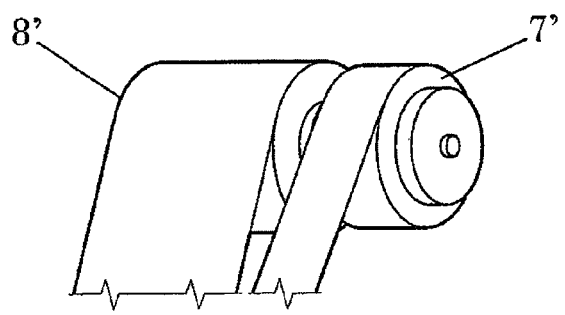
FIG. 4 shows a schematic perspective view of a part of the equipment comprising the film feed reels, depicting the longitudinal heat sealing phase thereof for obtaining the closing sheet of the invention.
Figure 4:
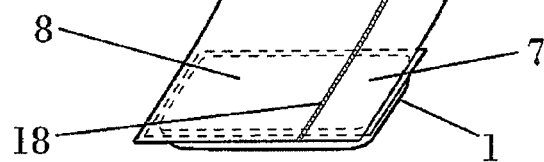

According to the invention, the first sheet (7) is obtained from a reel (7') and the second sheet (8) is obtained from a second reel (8'), being longitudinally joined, as is observed in FIG. 4, through a sealing line (18).

Figure 1:
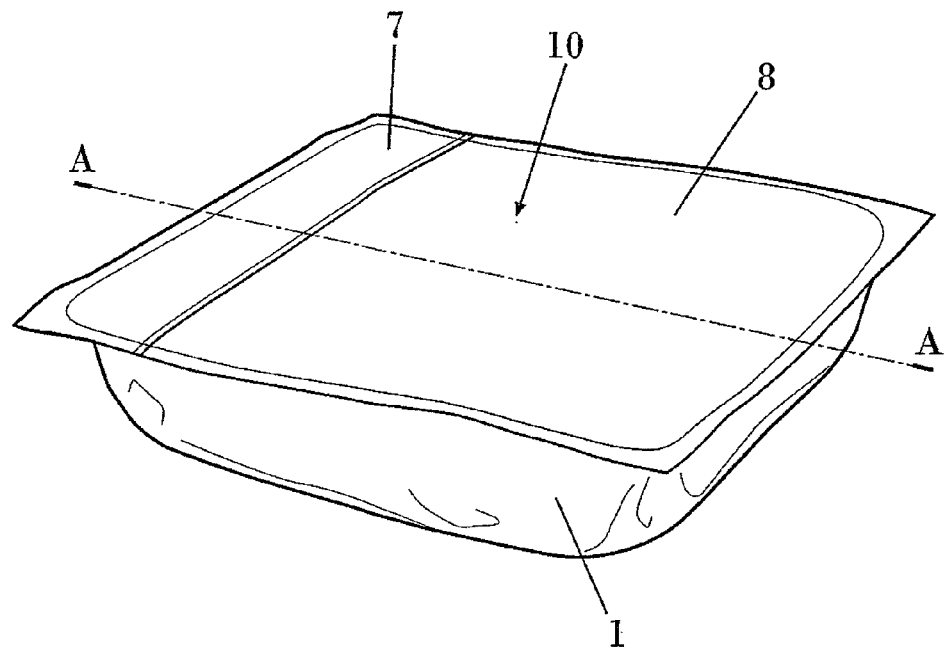
FIG. 1 shows a perspective view of the aseptic container object of the invention.
Figure 2:
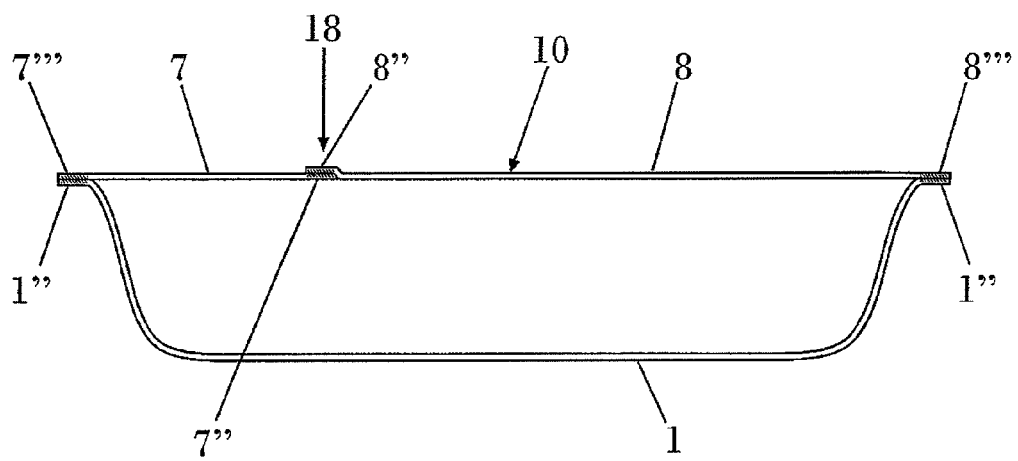
FIG. 2 shows a section according to line AA of the container of the previous figure.

As is observed in FIGS. 1 and 2, in the heat sealing line (18) the sheet (7) is overlapped with the sheet (8) through a first edge (7") and (8") of each of the sheets (7) and (8) respectively.

The sealing line (18) is preferably straight, and furthermore the closing sheet (10) has a quadrangular surface and the sealing line (18) is parallel to one of the sides thereof, as is depicted in the attached figures.

In other embodiments, not shown, the sealing line (18) can be curved, wavy or crooked and the closing sheet (10) can have a rectangular, oval or circular surface, depending on the shape of the container.

The second sheet (8) is preferably made of multilayer film, for example, polyester and/or polypropylene.

The closing sheet (10) can comprise a printed mark for identifying said closing sheet (10).

A second aspect of the invention relates to an aseptic container comprising a closing sheet (10) described above for containing sterilized objects for medical and/or pharmaceutical use.

The container comprises a body (1) of impermeable material, with the usual barrier characteristics and with a high micronage, defining a housing (6') configured to contain an object (6), preferably a unit container, free of microorganisms.

According to the invention the closing sheet (10) is configured to seal the housing (6'), perimetric edges of said closing sheet (10) being heat sealed to outer edges (1") of the body (1) of the container in its entire perimeter. The perimetric edges of the closing sheet are formed by a second edge (7''') and (8'''), of each of the sheets (7) and (8) respectively.

On the other hand, the body (1) of the container is configured to be obtainable from a multilayer film, for example of polyester and/or polypropylene, the housing (6') being defined by means of forming said body (1), for example, by thermopressure, blowing or by molding.

The second sheet (8) is preferably made of a material compatible for welding to the body (1), comprising for example a layer of polyethylene for sealing.

The second sheet (8) can be made of the same material as the body (1).

The surface of the first sheet (7) is configured to allow a passage of an amount of ethylene oxide sufficient to sterilize the housing (6') and the object (6) contained in the container.

The possibility is contemplated that the aseptic container comprises easy opening means existing in the containers of the state of the art configured to allow a removal of the closing sheet (10) by a user without additional means for opening the container.

The container can likewise comprise an identifying mark for identifying the object (6) contained in the container, made previously in the film of impermeable material or during the manufacture of the container.

A third aspect of the invention relates to equipment for obtaining an aseptic container described above, comprising a frame (3), as well as a lower reel (1') comprising an impermeable material configured to obtain a body (1) of the container, a plurality of clamps (2) configured to hold two opposite perimetric edges of a sheet of the material of the lower reel (1'), a forming mold (4), which can be actuated by means of pneumatic cylinders or mechanically (13), configured to thermoform a housing (6') in the body (1).

The equipment can comprise a vacuum pump (5) configured to perform vacuum in a face of the body (1) opposite to the closing sheet (10).

The equipment further comprises a first reel (7') comprising a film of material that is permeable to ethylene oxide and a second reel (8') comprising a film of impermeable material.

The equipment comprises sealing jaws (9) configured to heat seal a longitudinal edge of the film of permeable material of the first reel to a longitudinal edge of the film of impermeable material of the second reel, through a sealing line, to form a closing sheet (10) comprising a first sheet (7) of material that is permeable to ethylene oxide and a second sheet (8) of impermeable material, the first sheet (7) and the second sheet (8) being overlapped through a first edge (7") and (8"), respectively, forming the mentioned sealing line (18).

Figure 7:
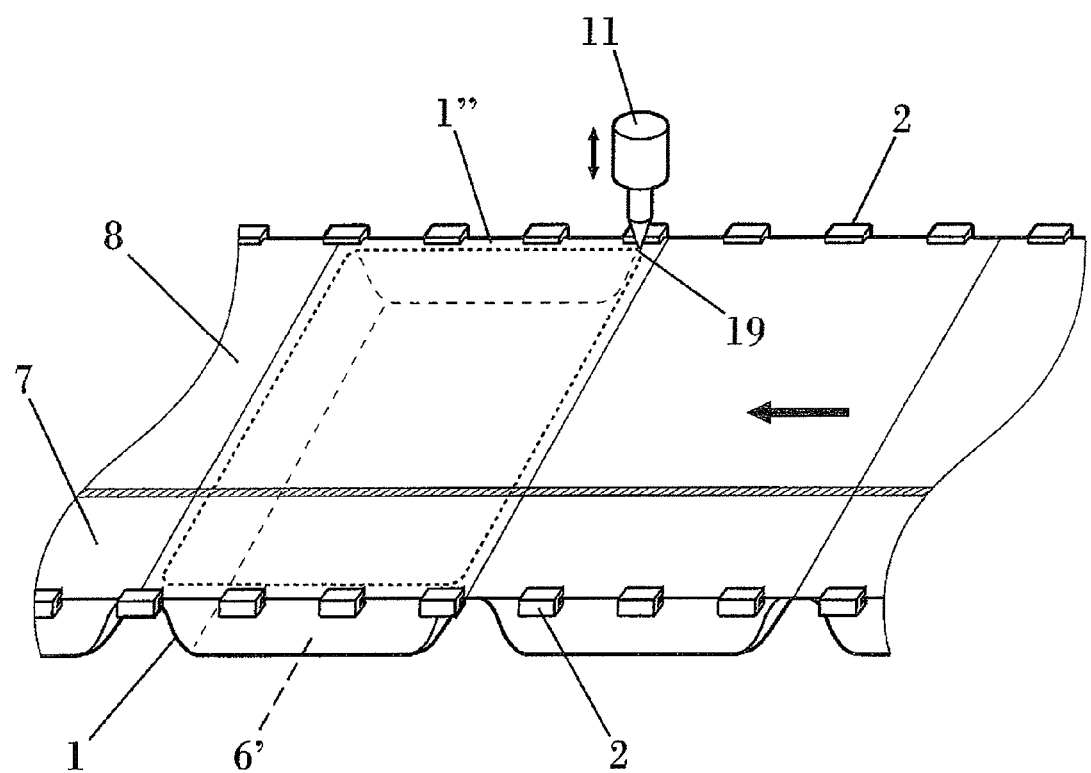
FIG. 7 is a schematic perspective view of a welding device.
Figure 8:
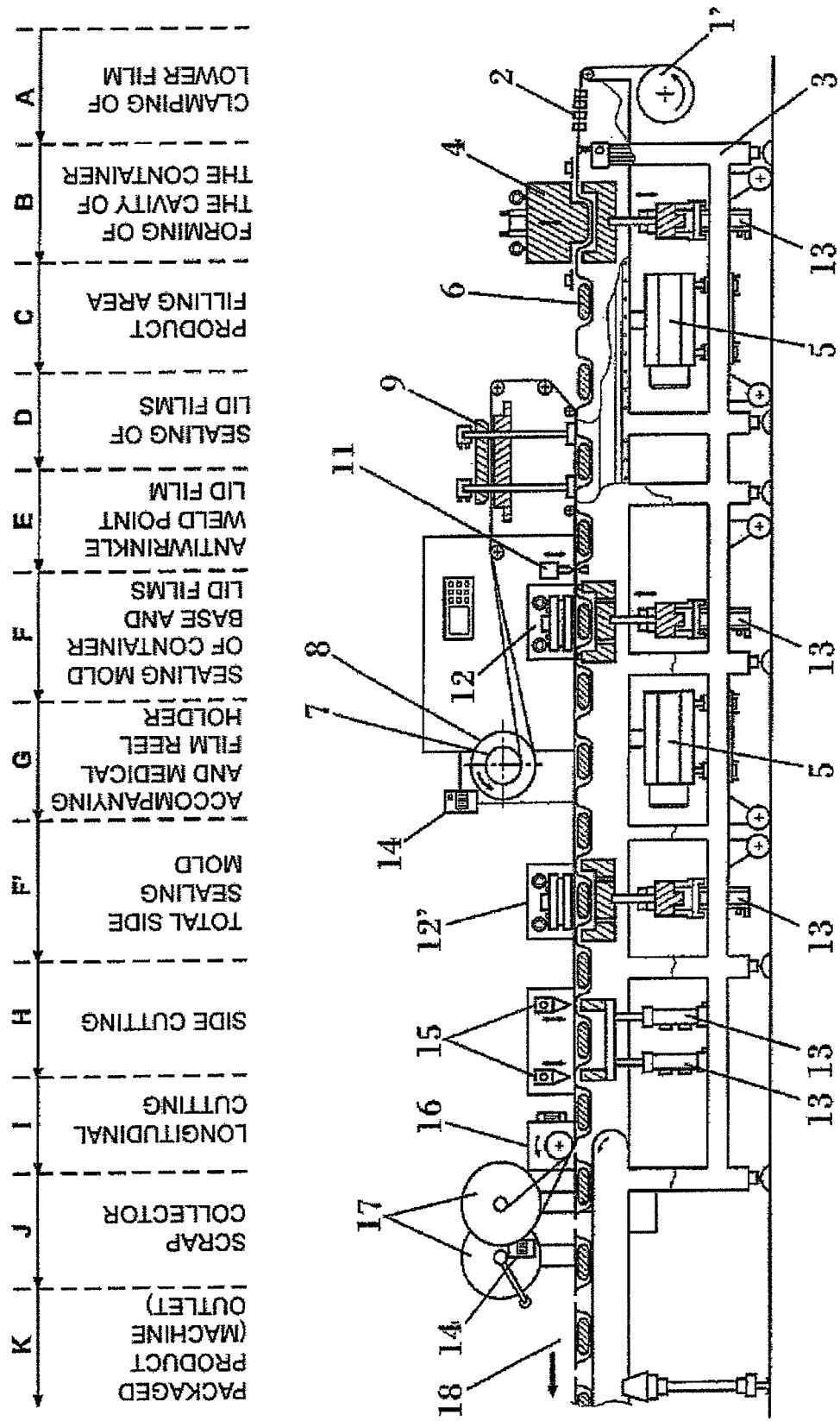
FIG. 8 shows an elevational view of the equipment for obtaining aseptic containers proposed by the invention.

The equipment also comprises a welding device (11) configured to heat weld the film of impermeable material of the second sheet (8'), in a plurality of weld points (19), to the film of impermeable material configured to obtain a containing body of the container in outer edge (1") of the body (1). The welding device (11) has been schematically depicted in FIG. 7.

Figure 3:
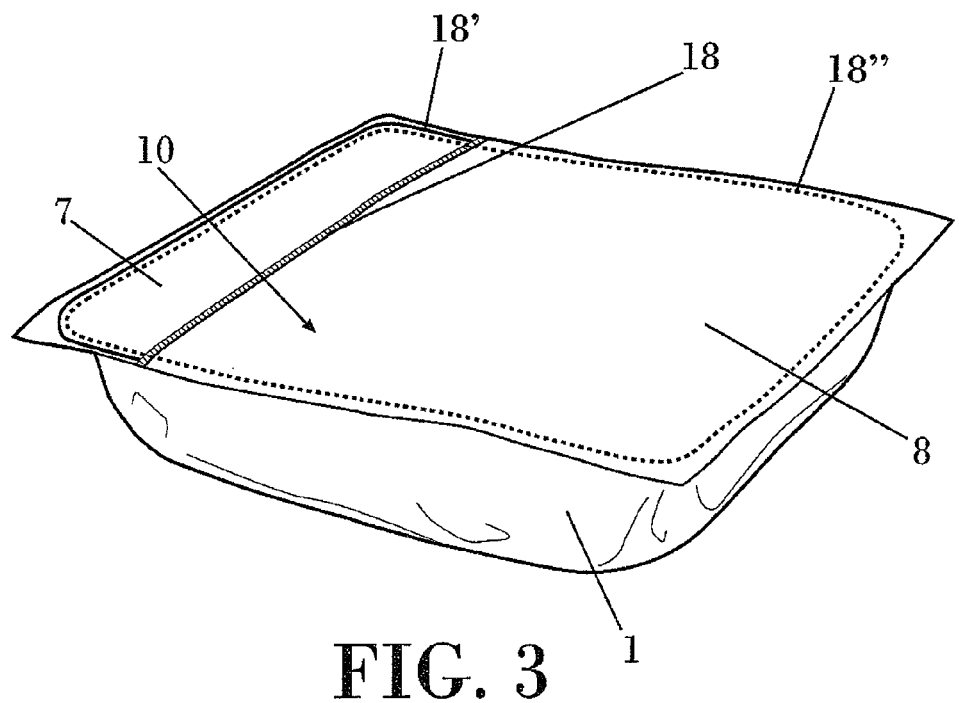
FIG. 3 shows a perspective view of the aseptic container object of the invention, in which the three sealings required to obtain it have been indicated approximately.
Figure 5:
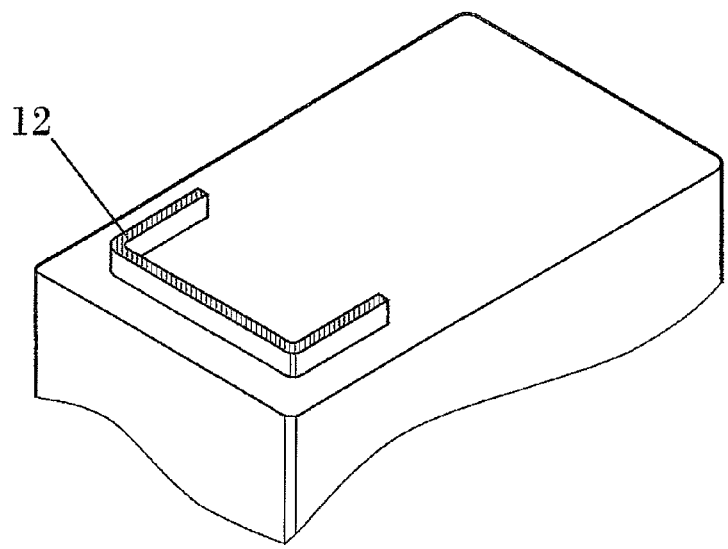
FIG. 5 shows a schematic perspective view of the first sealing mold comprised by the equipment of the invention.
Figure 6:
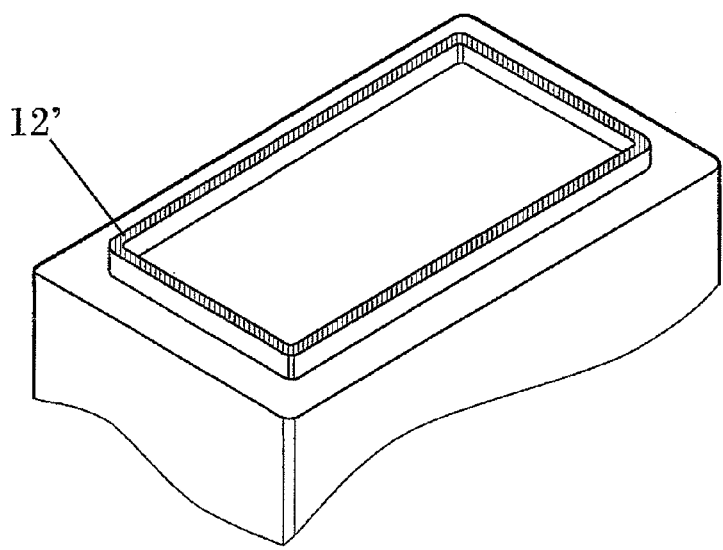
FIG. 6 is a schematic perspective view of the second sealing mold comprised by the equipment of the invention.

The equipment also comprises a first sealing mold (12) configured to heat seal the first sheet (7) to the outer edges (1") of the body (1), through a first area, at a first sealing temperature (carrying out a welding (18') schematically depicted in FIG. 3), and a second sealing mold (12') configured to heat seal the closing sheet (10) to the outer edges (1") of the body (1) at a second sealing temperature different from the first sealing temperature, comprising the heat sealing of the second edge (8''') of the second sheet (8) and of the second edge (7''') of the first sheet (7), carrying out a welding (18") schematically depicted in FIG. 3). The first sealing mold (12) has been schematically depicted in FIG. 5, whereas the second sealing mold (12') has been schematically depicted in FIG. 6.

The second sealing mold (12') can be configured to heat seal only the second edges (8''') of the second sheet (8) to the outer edges (1") of the body (1) at the mentioned second temperature. In this case, the first sealing mold (12) and the second sealing mold (12') can be configured to simultaneously heat seal the first sheet (7) and the second sheet (8) to the outer edges (1") of the body (1).

The possibility is contemplated that the equipment comprises a side cutting module (15) configured to cut surplus sides of the closed container, a longitudinal cutting module (16) configured to cut surplus longitudinal edges of the closed container, a device (17) configured to collect the surplus of film of the process and at least one conveyor belt (20) configured to move the containers in the equipment.

Finally, a fourth aspect of the invention relates to a method for obtaining an aseptic container described above with equipment like that described above, comprising the following steps:

holding with a plurality of clamps (2) two opposite perimetric edges of a film of impermeable material comprised in a lower reel (1'), thermoforming a housing (6') in the sheet of impermeable material forming a body (1), arranging an object (6) to be packaged in the housing (6'), heat sealing by means of sealing jaws (9) a longitudinal edge of a film of material that is permeable to ethylene oxide, comprised in a first reel (7'), to a longitudinal edge of a film of impermeable material, comprised in a second reel (8'), through a sealing line (18), forming a closing sheet (10) comprising a first sheet (7) of material that is permeable to ethylene oxide and a second sheet (8) of impermeable material, the first sheet (7) and the second sheet (8) being overlapped through a first edge (7") and (8") respectively, forming the mentioned sealing line (18)

heat welding in a plurality of weld points the film of impermeable material of the second reel (8') with the film of impermeable material of the lower reel (1'), in an outer edge (1") of the body (1) of the container, heat sealing, in a first sealing mold (12), a second edge (7''') of the first sheet (7) to the outer edges (1") of the body (1) of the container, through a first area, at a first sealing temperature, heat sealing, in a second sealing mold (12'), the perimetric edges of the closing sheet (10) to the outer edges (1") of the body (1) at a second sealing temperature different from the first sealing temperature, comprising the heat sealing of a second edge (8''') of the second sheet (8) and of a second edge (7''') of the first sheet.

It is contemplated as a possibility that the method comprises heat sealing, in the second sealing mold (12'), only the second edges (8''') of the second sheet (8) to the outer edges (1'') at the mentioned second temperature. The possibility is contemplated that the heat sealing in the second mold (12') and in the first mold (12) are carried out simultaneously.

Likewise, after heat sealing the closing sheet (10) to the body (1), the method can comprise the following steps:
- cutting surplus sides of the container in a side cutting module (15),
- cutting surplus longitudinal edges of the container in a longitudinal cutting module (16),
- collecting the surplus of the impermeable film and of the film that is permeable to ethylene oxide.

Finally, the aseptic container can be marked with an identifying mark for identifying the object (6) contained in the container.

In view of this description and set of figures, the person skilled in the art can understand that the embodiments of the invention which have been described can be combined in multiple ways within the object of the invention. The invention has been described according to several preferred embodiments thereof, but it will be evident for the person skilled in the art that multiple variations can be introduced in said preferred embodiments without exceeding the object of the claimed invention.

The invention claimed is:

1. Equipment for making an aseptic container,
the container comprising a closing sheet and a body (1) of impermeable material defining a housing (6') configured to contain an object (6), comprising a closing sheet (10) configured to seal the housing (6'), the perimetric edges of said closing sheet (10) being heat sealed to outer edges (1'') of the body (1) of the container in its entire perimeter, wherein the body (1) of the container is configured to be obtained from a sheet of multilayer film of polyester and/or polypropylene, the housing (6') being defined by means of thermoforming or molding of said body (1), the equipment comprising:
a frame (3),
a lower reel (1') comprising a film of impermeable material configured to obtain a body (1) of the container,
a plurality of clamps (2) configured to hold two opposite perimetric edges of the film of impermeable material of the lower reel (1'),
a forming mold (4) configured to thermoform a housing (6') in the reel of film of impermeable material which will form a body (1),
a first reel (7') comprising a film of material that is permeable to ethylene oxide,
a second reel (8') comprising a film of an impermeable material,
sealing jaws (9) configured to heat seal a longitudinal edge of the film of permeable material of the first reel to a longitudinal edge of the film of impermeable material of the second reel, through a sealing line, to form a closing sheet (10) comprising a first sheet (7) of material that is permeable to ethylene oxide and a second sheet (8) of impermeable material, the first sheet (7) and the second sheet (8) being overlapped through a first edge (7'') and (8''), respectively, forming the mentioned sealing line (18);
a welding device (11) configured to heat weld the film of impermeable material of the second reel (8'), in a plurality of weld points (19), to the film of impermeable material configured to obtain a containing body of the container in outer edge (1'') of the body (1),
a first sealing mold (12) configured to heat seal a second edge (7''') of the first sheet (7) to the outer edges (1'') of the body (1), through a first area, at a first sealing temperature,
a second sealing mold (12') configured to heat seal a second edge (8''') of the second sheet (8) to the outer edges (1'') of the body (1), through a second area, at a second sealing temperature different from the first sealing temperature.

2. Equipment according to claim 1, wherein the first sealing mold (12) and the second sealing mold (12') are configured to heat seal the first sheet (7) to the outer edges (1'') and the second sheet (8) to the outer edges (1'') simultaneously.

3. Equipment according to claim 1, wherein the second sealing mold (12') is configured to heat seal the second edge (7''') of the first sheet (7) to outer edges (1'') of the body (1), through a first area, at the second sealing temperature.

4. Equipment according to claim 1, further comprising:
a side cutting module (15) configured to cut surplus sides of the closed container,
a longitudinal cutting module (16) configured to cut surplus longitudinal edges of the closed container,
a device configured to collect the surplus of film of the process;
at least one conveyor belt (20) configured to move the obtained containers in the equipment.

* * * * *